(12) United States Patent  
Liu et al.

(10) Patent No.: US 8,687,917 B2  
(45) Date of Patent: Apr. 1, 2014

(54) METHOD AND APPARATUS FOR REGISTRATION OF AN ATLAS TO AN IMAGE

(75) Inventors: Jimin Liu, Singapore (SG); Su Huang, Singapore (SG); Wieslaw Lucjan Nowinski, Singapore (SG)

(73) Assignee: Agency for Science, Technology and Research, Centros (SG)

( * ) Notice: Subject to any disclaimer, the term of this patent is extended or adjusted under 35 U.S.C. 154(b) by 960 days.

(21) Appl. No.: 11/919,833

(22) PCT Filed: May 2, 2006

(86) PCT No.: PCT/SG2006/000112
§ 371 (c)(1),
(2), (4) Date: Jan. 2, 2009

(87) PCT Pub. No.: WO2006/118548
PCT Pub. Date: Nov. 9, 2006

(65) Prior Publication Data
US 2009/0220171 A1   Sep. 3, 2009

Related U.S. Application Data

(60) Provisional application No. 60/676,850, filed on May 2, 2005.

(51) Int. Cl.
*G06T 3/00* (2006.01)
*G06K 9/20* (2006.01)
*G06K 9/32* (2006.01)

(52) U.S. Cl.
USPC ........................................... 382/282; 382/294

(58) Field of Classification Search
None
See application file for complete search history.

(56) References Cited

U.S. PATENT DOCUMENTS

| 5,633,951 A | 5/1997 | Moshfeghi |
| 5,951,475 A * | 9/1999 | Gueziec et al. ............... 600/425 |
| 5,956,418 A * | 9/1999 | Aiger et al. ................... 382/154 |
| 6,037,949 A * | 3/2000 | DeRose et al. ................ 345/582 |
| 6,594,378 B1 | 7/2003 | Li et al. |
| 6,608,631 B1 | 8/2003 | Milliron |
| 6,611,615 B1 | 8/2003 | Christensen |

(Continued)

FOREIGN PATENT DOCUMENTS

| WO | WO 97/30652 A1 | 8/1997 |
| WO | WO0101346 A1 | 1/2001 |

OTHER PUBLICATIONS

"Quantifying Small Changes in Brain Ventricular Volume Using Non-rigid Registration" Mark Holden, Julia A. Schnabel, Derek L. G. Hill MICCAI '01 Proceedings of the 4th International Conference on Medical Image Computing and Computer-Assisted Intervention pp. 49-56.*

(Continued)

*Primary Examiner* — Michelle Entezari
(74) *Attorney, Agent, or Firm* — Wood, Phillips, Katz, Clark & Mortimer

(57) ABSTRACT

A method (100) and an apparatus (200) are disclosed for registering an input image and an atlas. The atlas is warped (130) using non-rigid registration. In particular, boundary displacements of structures in the atlas are calculated (132) which register those structures with equivalent structures in the input image. The boundaries of structures in the atlas are then warped (133) according to their respective boundary displacements using topology preserving propagation of boundary points of the structures.

15 Claims, 11 Drawing Sheets

(56) References Cited

U.S. PATENT DOCUMENTS

| | | | |
|---|---|---|---|
| 6,633,686 B1 | 10/2003 | Bakireioglu et al. | |
| 7,388,584 B2* | 6/2008 | Kase | 345/424 |
| 7,734,059 B2* | 6/2010 | Kase et al. | 382/100 |
| 8,321,150 B2* | 11/2012 | Taylor | 702/19 |
| 8,554,490 B2* | 10/2013 | Tang et al. | 702/19 |
| 2001/0002131 A1* | 5/2001 | DeRose et al. | 345/423 |
| 2001/0036302 A1 | 11/2001 | Miller | |
| 2003/0228042 A1* | 12/2003 | Sinha | 382/131 |
| 2004/0143426 A1* | 7/2004 | Stewart et al. | 703/2 |
| 2004/0257362 A1* | 12/2004 | Venkataraman et al. | 345/420 |
| 2005/0007368 A1* | 1/2005 | Doi et al. | 345/441 |
| 2005/0074153 A1* | 4/2005 | Pedrizzetti et al. | 382/128 |

OTHER PUBLICATIONS

Arad, N., Dyn, N., Reisfeld, D., and Yeshurin, Y., "Image warping by radial basis functions: application to facial expressions", CVGIP: Graphical Models and Image Processing, vol. 56, No. 2, pp. 161-172 (pp. 1-22 of attached document), 1994.

Bookstein, F.L., "Principal warps: thin-plate splines and decomposition of deformations", IEEE Transactions on Pattern Analysis and Machine Intelligence, vol. 11, No. 6, pp. 567-585, Jun. 1989.

Bookstein, F.L., "Landmark methods for forms without landmarks: Morphometrics of group differences in outline shape", Medical Image Analysis, (Jul. 1996) vol. 1, No. 3, pp. 225-243, 1997.

Bookstein, F.L., "Landmark methods for forms without landmarks: localizing group differences in outline shape", mmbia, pp. 279-289, Proc. Workshop on Mathematical Methods in Biomedical Image Analysis (MMBIA'96), IEEE, 1996.

Chan, Kwai Hung, and Lau, Rynson W.H., "Contour-based warping, CVGIP: Graphical Models and Image Processing", vol, 60, No. 5, pp. 331-348, 1998.

Chui, H., and Rangarajan, A., "A new algorithm for non-rigid point matching", IEEE Conference on Computer Vision and Pattern Recognition (CVPR), vol. 2, No. 1, pp. 44-51 (pp. 1-8 of attached document), 2000.

Frederick, C., and Schwartz, E.L., "Vision: Conformal image warping", IEEE Computer Graphics and Applications, vol. 10, No. 2, pp. 54-61, 1990.

Kanai, T., Suzuki, H., and Kimura, F., "Three-Dimensional Geometric Metamorphosis Based on Harmonic Maps", The Visual Computer, vol. 14. No. 4, pp. 166-176, 1998.

Rohr, K., Fornefett, M., and Stieh, H.S., "Spline-based elastic image registration: integration of landmark errors and orientation attributes", Computer Vision and Image Understanding, vol. 90, No. 2, pp. 153-168, 2003.

Warfield, Simon K., et al., "Real-Time Biomechanical Simulation of Volumetric Brain Deformation for Image Guided Neurosurgery", Proceedings of the 2000 ACM/IEEE conference on Supercomputing, Nov. 5-10, 2000, Dallas, Texas, IEEE Computer Society, pp. 1-16, 2000.

Wolberg, G., "Image morphing: a survey", The Visual Computer, vol. 14, No. 8/9, pp. 360-372, 1998.

Buhmann, M.D., "Radial basis functions: theory and implementations", New York: Cambridge University Press, 2003, pp. 11-35.

Klette, R. and Zamperoni, P., "Handbook of image processing operators", Chichester; New York: J. Wiley & Sons, 1996, pp. 26-37.

Christensen et al, "Volumetric Transformation of Brain Anatomy", IEEE Transactions on Medical Imaging, vol. 16, No. 6, Dec. 1997, pp. 867-877.

Zhu, Qing-hong, Chen, Yan and Kaufman, Arie, "Real-time Biomechanically-based Muscle Volume Deformation using FEM", Computer Graphics Forum, 17: pp. 275-284.

Liu, Jimin, Su, Huang, Eng, Thiam Yeo, and Nowinski, Wieslaw L., "Registration of brain atlas to MR images using topology preserving front propagation", Journal of Signal Processing Systems, 55(1): pp. 209-216.

"Deformable Associate Net Approach for Chest CT Image Segmentation"; Liu et al., Biomedical Imaging Lab, Bioinformatics Institute, Singapore 10 pages.

"Volumetric Object Modeling for Surgical Simulation", Gibson et al., Medica Image Analysis (1998) vol. 2, No. 2, pp. 121-132.

"Using Linked Volumes to Model Object Collisions, Deformation, Cutting, Carving, and Joining", Frisken-Gibson, IEEE Transactions on Visualization and Computer Graphics, vol. 5, No. 4, Oct.-Dec. 1999 pp. 333-348.

Correspondence—"Detection of 3-D Simple Points for Topology Preserving Transformations with Application to Thinning" Saha et al., IEEE Transactions on Pattern Analysis and Machine Intelligence, vol. 16, No. 10, Oct. 1994.

"Image Registration Based on Boundary Mapping", Davitzikos et al., IEEE Transactions on Medical Imaging, vol. 15, No. 1, Feb. 1996 (See whole document, in particular: Abstract; p. 112, Right column, Lines 11-15; p. 113, left column, lines 10-16 (document unavailable)).

"Registration of 3D Intraoperative MR Images of the Brain Using a Finite Element Biomechanical Model", Ferrant et al., IEEE Transactions on Medical Imaging, vol. 20, pp. 1384-1397, 2001 (See whole document, in particular: Abstract p. 2, right column, lines 23-42 (document unavailable)).

"A Review of Medical Image Registration", Maurer, Jr. Et al. Jan. 28, 1993 (See whole document (document unavailable)).

European Communication, Nov. 16, 2009—European Patent Office.

Szeliski R et al: "Matching 3-D Anatomical Surfaces with Non-Rigid Deformations using Octree-Splines", International Journal of Computer Vision, Kluwer Academic Publishers, Norwell, US. vol. 18, No. 2, May 1, 1996, pp. 171-186, XP000620153.

Kostelec, Peter J et al: "Multiresolution elastic image registration", Medical Physics, AIP, Melville, NY, US. vol. 25, No. 9, Sep. 1, 1998, pp. 1593-1604, XP012010559.

Musse O et al: "Fast deformable matching of 3D images over multiscale nested subspaces. Application to atlas-based MRI segmentation". Pattern Recognition, Elsevier, GB, vol. 36, No. 8, Aug. 1, 2003, pp. 1881-1899, XP004420923.

European Examination Report dated Aug. 10, 2012 for corresponding European Application 06 733 555.4.

Thompson, P. et al., "A surface-based Technique for Warping Three-Dimensional Images of the Brain", IEEE Transactions on Medical Imaging, IEEE Service Center, Piscataway, NJ, US, vol. 15, No. 4, Aug. 1, 1996, 402-417; XP000629472.

* cited by examiner

METHOD AND APPARATUS FOR REGISTRATION OF AN ATLAS TO AN IMAGE

FIELD OF THE INVENTION

The present invention relates generally to image deformation and, in particular, to image deformation where an atlas is registered to an image in a manner such that the topology of objects in the atlas is preserved.

BACKGROUND

Image deformation is an operation often performed in computer graphics. One application where image deformation is particularly useful is where objects in different images have to be registered, for example, to register objects in an atlas with objects obtained through magnetic resonance (MR) imaging. More specifically, in the field of neurosurgery a three-dimensional brain atlas is registered onto a volumetric MR image. Following the registration of the atlas and the brain image, brain functional image analysis, image-guided neurosurgery, and model-enhanced neuroradiology are facilitated through the resulting combined image.

Existing methods for image registration can be broadly classified into two classes, namely intensity based image registration and feature based image registration. In methods using intensity based image registration a transformation between two input images is sought that maximizes some intensity similarity measure between the two images. Such methods are easily automated as the transformation is derived directly from the intensity values of the image data when applied to the similarity measure. A substantial challenge, however, is the translation of an image-similarity function to a desired anatomic correspondence. In addition, a large amount of evenly distributed features confronts these methods with an extremely large search space and criterion landscapes with many local minima, leading to computing cost increase and precision degrading.

Compared to intensity based image registration methods, feature based image registration methods do not work with the image data directly. Feature based image registration methods operate by inserting an intermediate step wherein a set of structure-related homologous features are extracted. It is the matching of these structure-related homologous features which is then used for registration. The features used for guiding the deformation vary from individual points, lines, contours, surface patches, entire parameterized surfaces, and particular objects. The reliance on structural information makes these methods more anatomically relevant. However, the challenge with these methods lies with obtaining a sufficiently large number of features automatically to drive the deformation.

A need therefore exists for a registration method which does not require particular structures to be extract, and which preserves topology of structures during deformation of such structures.

SUMMARY

According to a first aspect of the invention, there is provided a method of non-rigidly registering an atlas with an image. The atlas comprises labels, and each label corresponds to either a labeled structure or an unlabeled structure. The method comprises the steps of:

calculating a boundary displacement of at least one structure in the atlas to register that structure with an equivalent structure in the image; and warping the boundary of the structure in the atlas according to the boundary displacement using topology preserving propagation of boundary points of the structure.

According to another aspect of the present invention, there is provided an apparatus for implementing the aforementioned method.

According to another aspect of the present invention there is provided a computer program product including a computer readable medium having recorded thereon a computer program for implementing the methods described above.

Other aspects of the invention are also disclosed.

BRIEF DESCRIPTION OF THE DRAWINGS

One or more embodiments of the present invention will now be described with reference to the drawings, in which.

DETAILED DESCRIPTION

Figure 1:
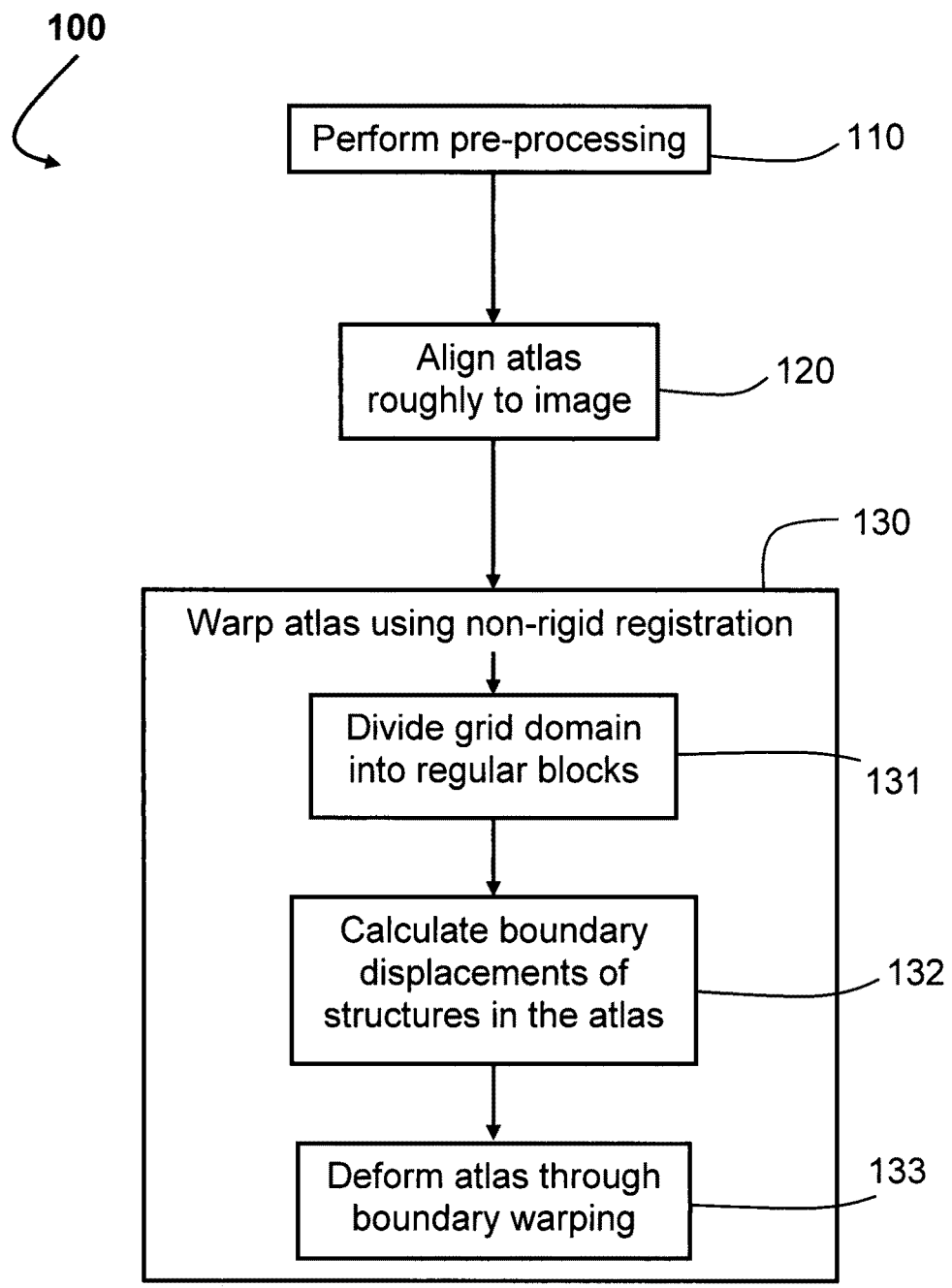
FIG. 1 shows a schematic flow diagram of a method of registering an input image and an atlas.

Where reference is made in any one or more of the accompanying drawings to steps and/or features, which have the same reference numerals, those steps and/or features have for the purposes of this description the same function(s) or operation(s), unless the contrary intention appears.

FIG. 1 shows a schematic flow diagram of a method 100 of registering an input image I(x) and an atlas A(x). The image I(x) and the atlas A(x) are volumetric images defined in a grid domain $D=[1 \ldots n_1] \times [1 \ldots n_2] \times [1 \ldots n_3]$ wherein the parameters $n_1$, $n_2$ and $n_3$ specify the size of the atlas A(x). Atlas $A(x) \in L = \{0, 1, 2, \ldots, I\}$, wherein L are labels defined within the atlas A(x), and I indicates the number of labels defined in the atlas A(x). Each nonzero label L corresponds to a structure, whereas the label L=0 represents unlabeled structures.

The values of the image I(x) at each three-dimensional grid point x, or voxel, may represent any element property. In a preferred implementation the image I(x) is formed from sampled intensity values, for example generated using 3-D medical scanners or computed tomography (CT) devices.

Figure 2:
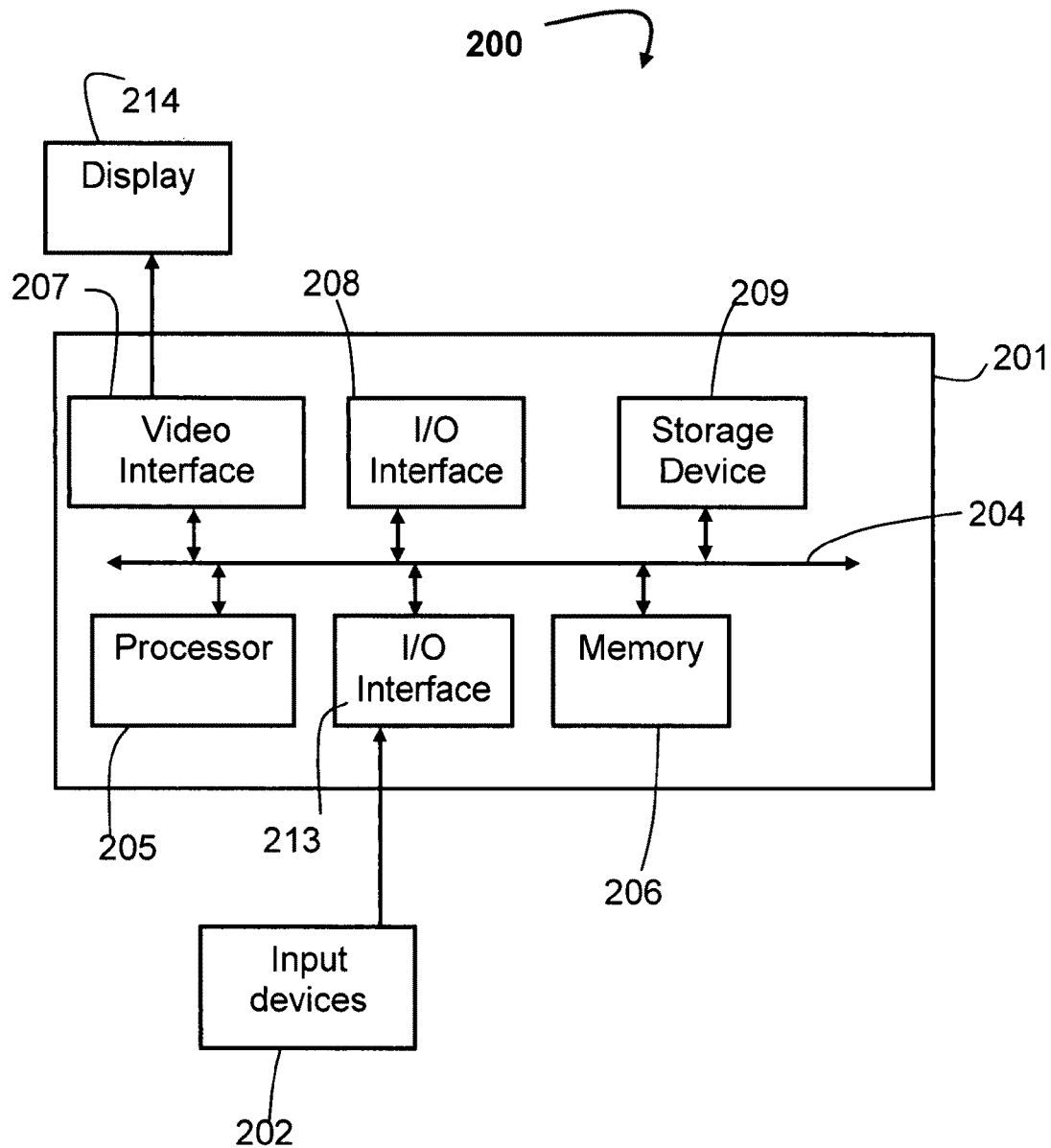
FIG. 2 shows a schematic block diagram of a computer system upon which the method shown in FIG. 1 may be practiced.

The method 100 of registering the input image I(x) and the atlas A(x) is preferably practiced using a computer system 200, such as that shown in FIG. 2 wherein the steps of method 100 is implemented as software, such as an application program, executing within the computer system 200. In particular, the steps of the method 100 are effected by instructions in the software that are carried out by the computer system 200. The software may be stored on a computer readable medium. The software is loaded into the computer system 200 from the computer readable medium, and then executed by the computer system 200. A computer readable medium having such software or computer program recorded on it is a computer program product. The use of the computer program product in the computer system 200 preferably effects an advantageous apparatus for registering the input image I(x) and the atlas A(x).

The computer system 200 is formed by a computer module 201, input devices 202 such as a keyboard and/or a pointing device, and a display device 214. The computer module 201 typically includes at least one processor unit 205, and a memory unit 206. The module 201 also includes a number of input/output (I/O) interfaces including a video interface 207 that couples to the video display device 214, and an I/O interface 213 for the input devices 202. A storage device 209 is provided and typically includes a hard disk drive. A CD-ROM drive (not illustrated) may be provided as a non-volatile source of data. The components 205 to 213 of the computer module 201, typically communicate via an interconnected bus 204 and in a manner which results in a conventional mode of operation of the computer system 200 known to those in the relevant art.

Typically, the application program is resident on the storage device 209 and read and controlled in its execution by the processor 205. Intermediate storage of the program and any data may be accomplished using the memory 206, possibly in concert with the storage device 209. In some instances, the application program and atlas A(x) may be supplied to the user encoded on a CD-ROM, and read via a corresponding drive (not illustrated), or alternatively may be read by the user from a network via a modem device. Still further, the software can also be loaded into the computer system 200 from other computer readable media. The term "computer readable medium" as used herein refers to any storage or transmission medium that participates in providing instructions and/or data to the computer system 200 for execution and/or processing.

Referring again to FIG. 1, the method 100 of registering the input image I(x) and the atlas A(x) starts in step 110 where the image I(x) is pre-processed. Pre-processing typically includes removal of features in the image I(x) which are not part of the object modelled in the atlas A(x).

Step 120 follows where the atlas A(x) is roughly aligned to the image I(x) through a global affine transformation. The atlas A(x) is then in step 130 warped using non-rigid registration in order to register the atlas A(x) with the image I(x). The non-rigid registration of step 130 is described in more detail below.

A preferred application of method 100 is in the medical field, and in particular the field of neurosurgery. In that application the atlas A(x) is a brain atlas and the image I(x) is obtained through magnetic resonance imaging (MRI). MRIs are able to capture a three dimensional image of the internal structure of a patient's body at high resolution such as 0.8× 0.8×1.2 mm$^3$. The preferred brain atlas used is that which was published by Nowinski W. L. and Belov D. in the publication *Neuroimage*, vol. 20 (1), 2003, pp. 50-57, in an paper entitled "*The Cerefy Neuroradiology Atlas: a Talairach-Tournoux atlas-based tool for analysis of neuroimages available over the Internet*", where a high resolution brain atlas was generated by interpolation of the digital Talairach-Tournoux (TT) atlas. That brain atlas has 137 different structures, i.e. I=137.

Figure 4A:
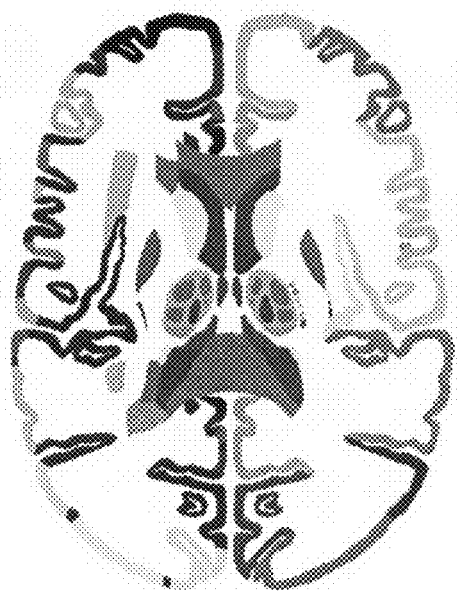
FIG. 4A shows a slice of a Talairach-Tournoux brain atlas.
Figure 4B:
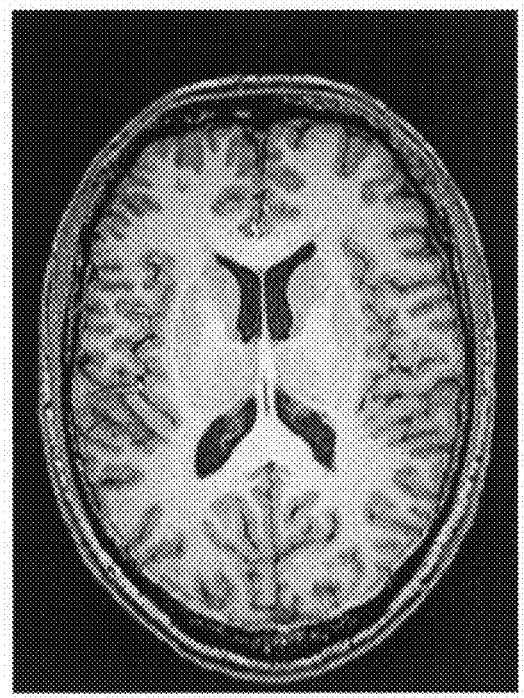
FIG. 4B shows a two-dimensional image obtained through magnetic resonance imaging.

FIG. 4A shows a representation of a slice of the Talairach-Tournoux brain atlas. FIG. 4B shows a two-dimensional MRI slice of a patient's brain.

In step 110 the MRI brain image I(x) is pre-processed by removal of the scalp and skull. Preferably morphological operations and connected component analysis are used to remove the scalp and skull from the MRI brain image I(x).

Referring again to FIG. 1, the non-rigid registration of step 130 where the atlas A(x) is warped in order to register the atlas A(x) with the image I(x) is now described in more detail. Step 130 starts in sub-step 131 where the grid domain D is divided into a set of regular blocks, namely, hexahedrons. In particular, the grid domain D is divided into a set of regular blocks $\{B(p_1), B(p_2), \ldots, B(p_m)\}$, with each block having the dimensions $L_1 \times L_2 \times L_3$. Block $B(p_i)$ is a hexahedron having a centre point $p_i$ (i=1, 2, ... m). All the centre points $\{p_1, p_2, \ldots, p_m\}$ form an adjunct block set $\{B'(q_1), B'(q_2), \ldots, B'(q_n)\}$ where centre points $q_j$ (j=1, 2, ... n) of block $B'(q_j)$ are vertexes of block $B(p_i)$, and vertexes of block B' are centre points $p_i$ of blocks B.

Figure 5:
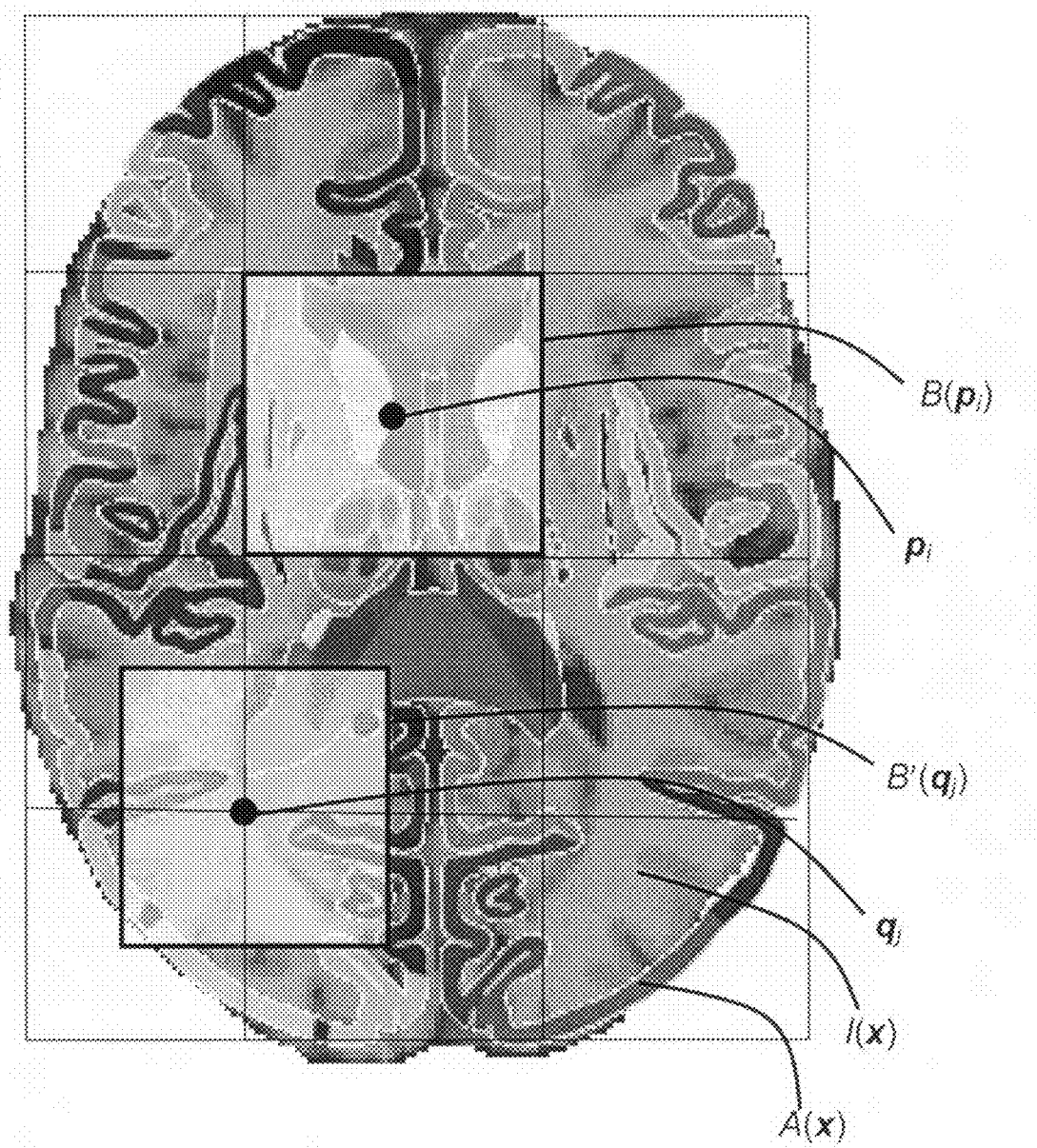
FIG. 5 illustrates a slice of a brain atlas aligned to a brain image, as well as a 2-dimensional portion of the grid of a grid domain.

FIG. 5 illustrates an atlas slice superimposed to a slice of an MRI brain image I(x). Also illustrated in FIG. 5 is a 2-dimensional portion of the grid of the grid domain D. Block $B(p_i)$ is a hexahedron having centre point $p_i$. Block $B'(q_j)$ is a block (hexahedron) from the adjunct block set and having centre point $q_j$.

Referring again to FIG. 1, following sub-step 131 a block matching method is then used in sub-step 132 to calculate a boundary displacement of each structure in the atlas A(x). In the preferred application where the method 100 is used to align a brain atlas A(x) with an MRI brain image I(x), it is impossible to use a simple function, such as the affine transformation, to describe the one-to-one correspondence between the (general) brain atlas A(x) and the brain image I(x) from a particular patient. This is due to the complexity and variability of brain structures.

Sub-step 132 operates by first calculating the displacement $dp_i$ of each block center point $p_i$ by maximizing a block similarity measure $S(A|B(p_i), I|B(p_i+dp_i))$ of atlas block A|B$(p_i)$ within block $B(p_i)$ and image block I|B$(p_i+dp_i)$ within the block $B(p_i+dp_i)$ as follows:

$$dp_i = \arg\max_{|dp_{ij}| < L_j/2 (j=1,2,3)} [S(A | B(p_i), I | B(p_i + dp_i))] \quad (1)$$

Block $B(p_i+dp_i)$ is obtained by translating block $B(p_i)$ in grid domain D with the displacement $dp_i=(dp_{i1}; dp_{i2}; dp_{i3})$. The displacement $dp_i$ of each block B is restricted such that the displacement $dp_i$ may not exceed half the block edge length in each direction, that is:

$$|dp_{ij}| < L_j/2 \ (j=1,2,3). \quad (2)$$

To calculate the block similarity measure $S(A|B(p_i), I|B(p_i+dp_i))$, suppose that all points x of the atlas A(x) in block $B(p_i)$ are classified into one of k subset $O_1, O_2, \ldots, O_k$ according to their labels L. That is:

$$O_t = \{x | x \in B(p_i), A(x) = I_t\} \ (t=1,2,\ldots k), \quad (3)$$

wherein $I_1, I_2, \ldots$, and $I_k$ are different atlas labels L. In this case, according to the intensity of the image $I(x)$, all points x of the image $I(x)$ in the displaced block $B(p_i+dp_i)$ are classified into one of k clusters $C_1, C_2, \ldots, C_k$ with intensity from low to high by using a fussy clustering method, such as the fussy clustering method disclosed in the article entitled "An adaptive spatial fuzzy clustering algorithm for 3-D MR image segmentation", IEEE Trans Med Imaging. 22 (9), pp. 1063-1075, 2003, by Alan W. C. L. and Hong Y.

For a given imaging modality, suppose that the average intensity of objects with labels $I_1, I_2 \ldots, I_k$ are sorted from low to high. it is then reasonable to assume that cluster $C_t$ corresponds to subset $O_t$. This allows the block similarity measure $S(A|B(p_i), I|B(p_i+dp_i))$ to be calculated as follows:

$$S(A \mid B(p_i), I \mid B(p_i + dp_i)) = \sum_{t=1}^{k} [\#[(O_t + dp_i) \cap C_t]/(\sigma_t + 1)] \quad (4A)$$

wherein # denotes the cardinality of a set, and $\sigma_t$ is the intensity variance of points x of image $I(x)$ within volume $O_t+dp_i$. Some structures can only be distinguished by their locations and morphologies, not by their intensities in the image $I(x)$. This is for example the case with all the gyrus on the cortical surface. The labels $I_1, I_2 \ldots, I_k$ of such structures are converted to one label L for the similarity measure S calculation.

The displacement dx of all points x on structure boundaries is then calculated as the interpolation of displacements $\{dp_1, dp_2, \ldots, dp_m\}$. For any point x, there exist a block $B'(q_j)$ such that $x \in B'(q_j)$. The block $B'(q_j)$ has 8 vertexes $\{p_{ij}\}$ (i=1, 2, ... 8) which are centre points of blocks $B(p_{ij})$, and the displacement dx of point x is calculated as:

$$dx = \frac{1}{8} \sum_{i=1}^{8} \left\{ \prod_{k=1}^{3} \left[ 1 + \frac{4}{L_k^2}(x_{ik} - x_{0k})(x_k - x_{0k}) \right] \right\} dp_i \quad (4B)$$

wherein $(x_{i1}, x_{i2}, x_{i3})$ denotes the coordinate of centre point $p_{ik}$ (i=1, 2, ..., 8), $(x_{01}, x_{02}, x_{03})$ indicates the coordinate of the centre point $q_j$ of block $B'(q_j)$, $dp_i$ is the displacement of centre point $p_i$ of block $B(p_i)$, and $(x_1, x_2, x_3)$ indicates the coordinates of the point x.

Figure 8A:
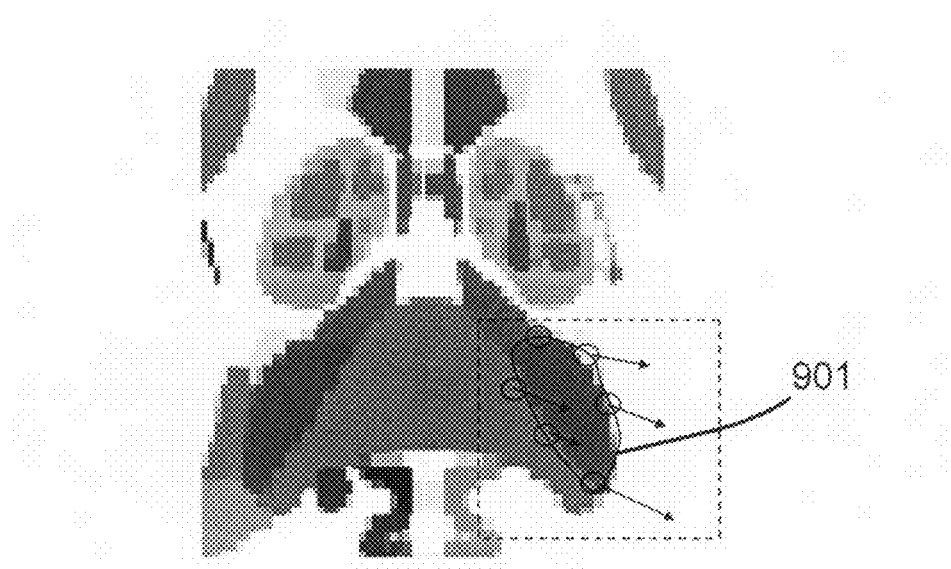
FIG. 8A illustrates a portion of the brain atlas slice shown in FIG. 5, the boundary of a structure, and its boundary displacement.

FIG. 8A illustrates a portion of the slice in brain atlas $A(x)$ shown in FIG. 5, that portion being a portion bounded by a single block B. Also illustrated is the boundary of a structure 901, and its boundary displacement.

Finally, in sub-step 133 the atlas $A(x)$ is deformed by boundary warping and using topology preserving front propagation. In particular, each structure is warped according to the boundary displacement of that structure determined in sub-step 132.

Figure 8B:
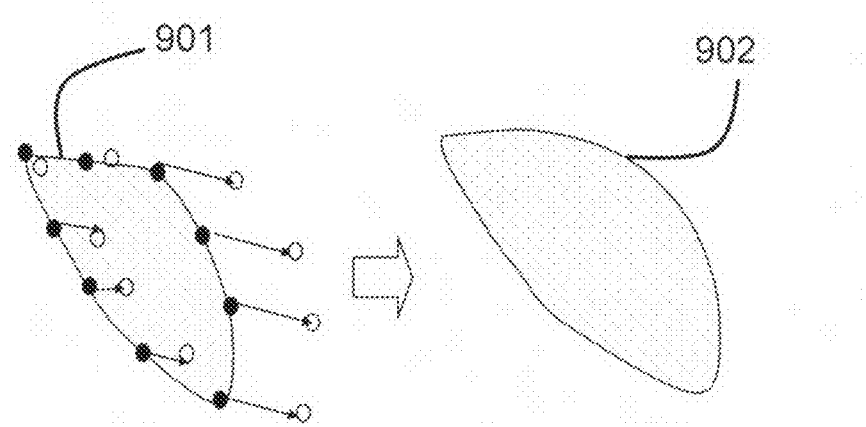
FIG. 8B illustrates the structure shown in FIG. 8A, the boundary displacement of that structure, and that structure after boundary warping.

FIG. 8B illustrates the structure 901 shown in FIG. 8A, together with its boundary displacement, and that structure 901 after boundary warping, providing structure 902.

In order to preserve the topology of structures within the atlas $A(x)$, regions and contours of structures within the atlas $A(x)$ may not overlap each other. This is a very natural requirement, since these regions and contours indicate different tissues or landmarks. Another requirement that has to be satisfied in order to preserve topology is that two line segments from the same contour may not intersect (except for their end points). This requirement indicates that the topological characteristic of a given region or contour does not change, and it is reasonable in cases when the general model correctly represent the topology relationships amongst considered tissues.

With regards to model deformation, in the prior art there generally exist two categories of methods to solve this boundary warping problem, those categories being surface based methods and volume based methods. The volume based methods are easy to implement, but are very computationally expensive, which makes these methods relatively slow. Surface based methods are faster. However, surface based methods of model deformation require a geometrical surface model to be generated, which is also time consuming.

Another method used which strictly does not fall within any one of the two model deformation categories identified above is to generate surfaces from sparse points. This method is also computationally expensive, especially when the number of points is large.

Figure 6A:
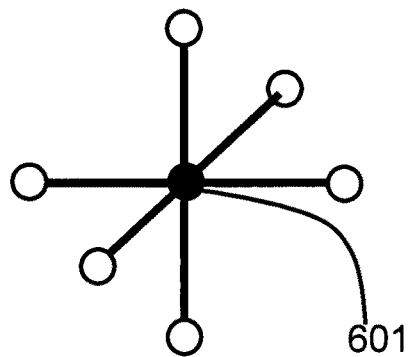
FIGS. 6A and 6B illustrate 6-connected and 26-connected neighbours respectively.
Figure 6B:
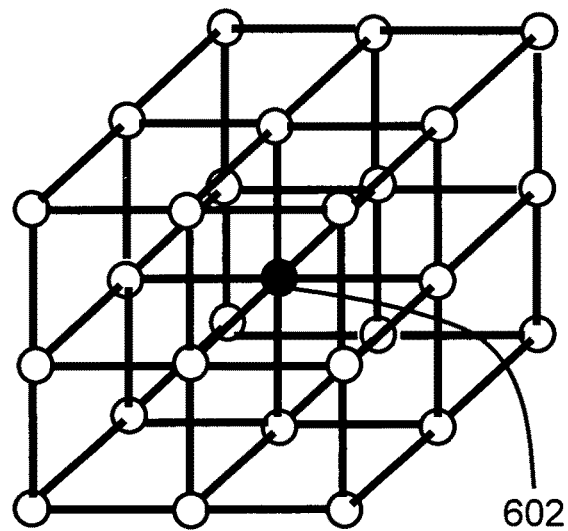

In view of the foregoing deficiencies exhibited by common model deformation methods, a front propagation approach is used in sub-step 133 to deform the atlas $A(x)$. In order to preserve topology, the concept of digital topology is adopted. A connectivity pair (6, 26) is chosen, that being 6-connectivity for objects and 26 for object counterparts. FIG. 6A shows a point 601 together with its 6-connected neighbours, whereas FIG. 6B shows a point 602 together with its 26-connected neighbours.

Let point P be a front point of a volume volume(P), which means that: $P \in volume(P)$. All points x in volume(P) have the same label L and are 6-connected. A point P is a front point of volume(P) when at least one 6-connected neighbour of point P is not labelled with the same label L as points in volume(P). A front is a set of 26-connected front points.

Since there are multiple fronts, and topology must be preserved during propagation of the front, it is difficult, if not impossible, to propose a physically meaningful continuous model to describe the front propagation used for the boundary warping. Therefore, instead of using a traditional continuous model, a digital front propagation method is directly adopted.

In the digital front propagation method, atlas deformation is achieved by adding points to and removing points from all volumes in a breadth first style. That is, each front is repeatedly advanced one step forward in turn until none of the fronts can propagate any further. The key principles of this digital front propagation method are front displacement update and single front one step forward propagation.

As an initial condition, the position $P.x=(P.x_1, P.x_2, P.x_3)$ and displacement $P.dx=(P.dx_1, P.dx_2, P.dx_3)$ of each front point P are known. After the front propagates one step forward, some front points P are removed, whereas some front points P are added to the volume volume(P) under consideration. As a result, a new front is defined by the changed volume(P). In order to advance the new front, it is needed to update the displacement P.dx of all front points P on the new front.

Let [P.x] indicate the grid point on the three dimensional grid to which the front point P is approximate to. Hence, with the position $P.x=(P.x_1, P.x_2, P.x_3)$, the grid point $[P.x]=([P.x_1], [P.x_2], [P.x_3])$ to which the position P.x is approximate to is the grid point [P.x] which satisfies the following condition for i=(1, 2, 3):

$$|[P.x_i]-P.x_i| \leq 0.5 \quad (5)$$

When [P.x]=[P.x+P.dx], that is the position of front point P before and after displacement is approximate to the same grid point, that front point P is considered to be non-active and can not propagate any further. Similarly, when [P.x]≠[P.x+P.dx], that is the position of front point P before and after displacement is not approximate to the same grid point, that front point P is considered to be active. Only active front point P propagate forward.

For each active front point P, a preceding point pre(P) and a succeeding point next(P) are determined. The position next (P).x of the succeeding point next(P) is determined by moving from the (current) position P.x of front point P along the displacement vector P.dx in a manner so that:

the grid point [next(P).x] is within the 26-connected neighbours of the grid point [P.x]; and the grid point [next(P).x] achieves the minimum distance from the line passing through positions P.x and P.x+P.dx.

Formally:

$$\mathcal{R}(P.x) = \left\{ \begin{array}{c} y \mid y = \underset{y}{\mathrm{argmin}}[d_1([y], P.x, p.x + P.dx) \mid y = P.x + \alpha P.dx, \alpha > 0], \\ d_2[P.x], [y] = 1 \end{array} \right\} \quad (6)$$

$$next(P).x = \underset{y \in \mathcal{I}(P.x)}{\mathrm{arg\,min}}\{d_3(P.x, y)\}, \quad (7)$$

$$nex(P).dx = (P.x + P.dx) - next(P).x$$

wherein the function $d_1(p_1, p_2, p_3)$ provides the minimum distance from point $p_1$ to the line segment through points $p_2$ and $p_3$;

the function $d_2([x],[y]) = \max\{|[x_i] - [y_i]| \; i=1, 2, 3\}$; and the function $d_3(x, y)$ provides the distance between the two points x and y.

The position pre(P).x of the preceding point pre(P) is determined in a manner similar to that of the succeeding point next(P) described above. The difference is that when the position pre(P).x is determined, movement is performed from the (current) position P.x of front point P along displacement vector −P.dx, in a manner so that grid point [pre(P).x] to which is the position pre(P).x of the preceding point pre(P) is approximate to is also a neighbour to grid point [P.x]. Also, the grid point [pre(P).x] has the minimum distance from the extended line passing through positions P.x and pre(P).x.

Figure 7A:
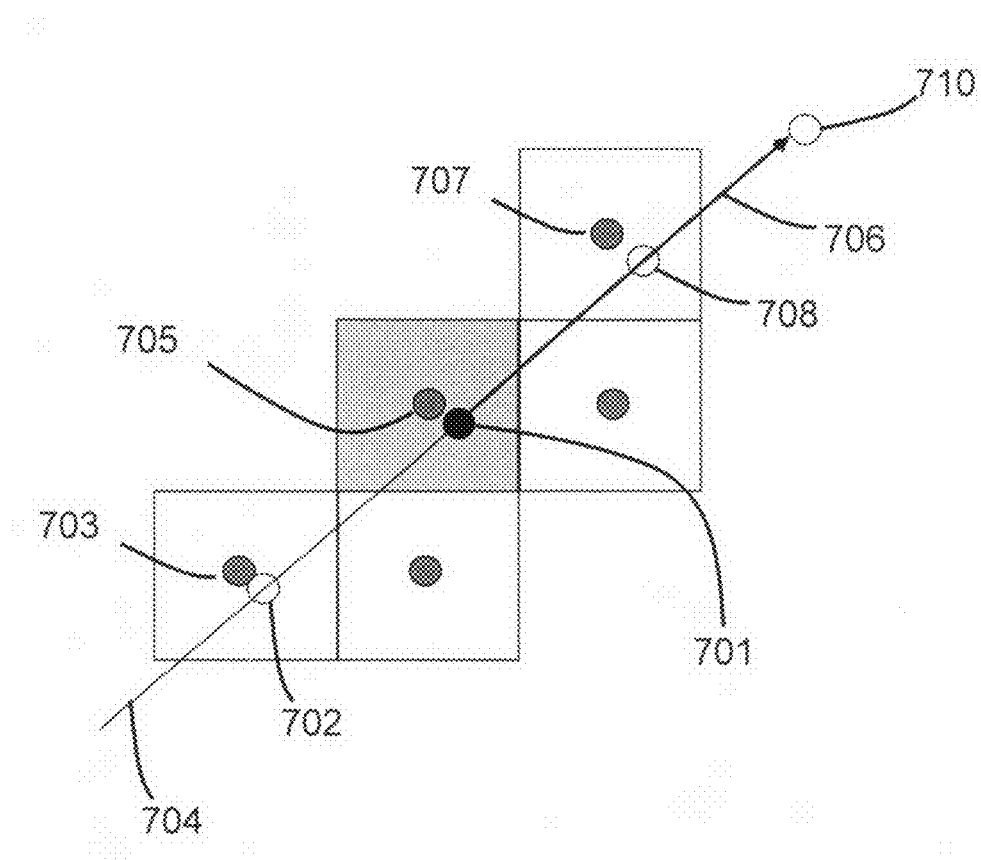
FIGS. 7A to 7C illustrate the displacement update of a new front point.

In order to illustrate the relationship between a front point P, its preceding point pre(P) and its succeeding point next(P), FIG. 7A illustrates a front point 701 having position P.x. The position P.x of the front point P relative to grid positions is also illustrated. In the illustration only two dimensions are shown for clarity. However, as would be clear from the description, the grid domain D is three-dimensional.

The grid point [P.x] to which the position P.x is approximate to is grid point 705. Vector 706 indicates the displacement P.dx calculated for front point P, which defines the target point 710 (P.x+P.dx) for front point P.

The position next(P).x of the succeeding point next(P) is then determined by moving from the (current) position P.x of front point 701 along the displacement vector 706 towards the target point 710. Point 708 is determined the succeeding point next(P), with the grid point 707 to which point 708 is approximate to being a 26-connected neighbour to the grid point 705. Point 708 has the minimum distance from the line passing through positions 701 and 710.

Similarly, the position pre(P).x of the preceding point pre (P) is determined by moving from the (current) position P.x of front point 701 along the displacement vector −P.dx. Point 702 is determined as the preceding point pre(P), with the grid point 703 to which point 702 is approximate to being a 26-connected neighbour to the grid point 705. Point 702 has the minimum distance from the extended line 704 passing through positions 701 and 710.

Now, consider a front including the front points $\{P_1, P_2, \ldots, P_n\}$. When the front advances, the new position Q.x and displacement Q.dx of a point Q, which is a 26-connected neighbour to at least one of the front points $\{P_1, P_2, \ldots, P_n\}$, and is calculated as follows:

If there are one or more front points $\{P_{i1}, P_{i2}, \ldots P_{ik}\}$ that propagate to grid position [Q.x] when the front is propagated by one step forward, i.e. $[next(P_{is}).x]=[Q.x]$ (s=1, 2, ... k), then the position Q.x and displacement Q.dx take the corresponding values of the succeeding point $next(P_{is})$ of front point $P_{is}$ that results in the minimum distance from the grid position $[next(P_{is}).x]$ to which the succeeding point $next(P_{is})$ is approximate to, to the line segment between points $P_{is}.x$ and $P_{is}.x+P_{is}.dx$. Hence, point Q results from propagating front point $P_{is}$ one step forward. Formally this is stated as:

$$s = \underset{s}{\mathrm{argmin}}\{d_1([next(P_{is}) \cdot x], P_{is} \cdot x, P_{is} \cdot x + P_{is} \cdot dx)\} \quad (8)$$

$$Q.x = next(P_{is}).x, Q.dx = next(P_{is}).dx \quad (9)$$

wherein the function $d_1(p_1, p_2, p_3)$ again provides the minimum distance from point $p_1$ to the line segment through points $p_2$ and $p_3$.

Figure 7B:
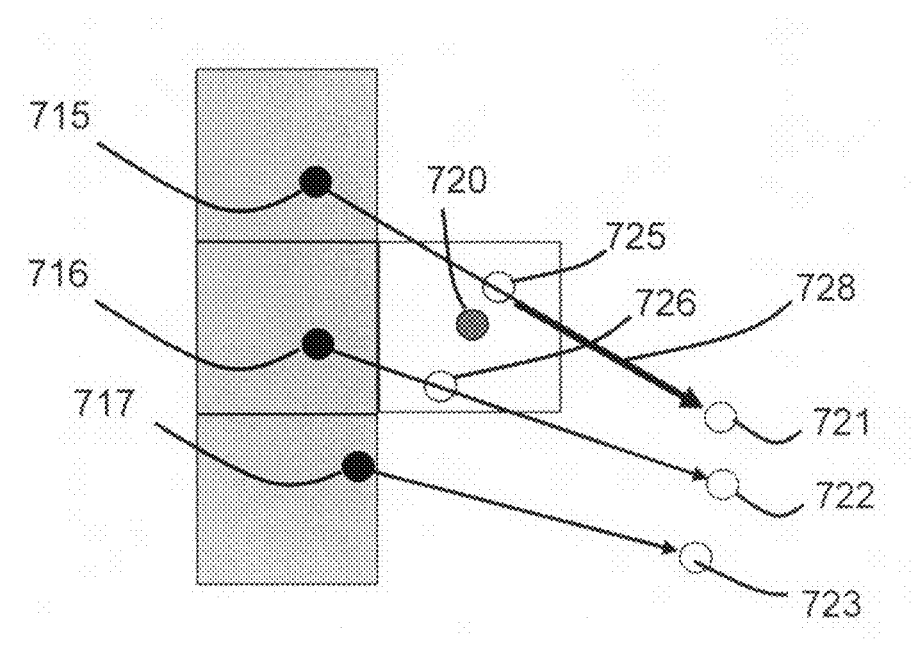

The above described scenario is illustrated in FIG. 7B. A front including three front points 715, 716 and 717 is shown. The front points 715, 716 and 717 have target points 721, 722 and 723 respectively. When the front is propagated by one step forward, front points 715 and 716 propagate to succeeding points 725 and 726 respectively. However, both of points 725 and 726 are approximate grid position 720, which corresponds to [Q.x]. As succeeding point 725 is closer to the grid position 720 than the succeeding point 726, the position Q.x and displacement Q.dx take the values of the succeeding point 725 of front point 715. The displacement Q.dx is indicated as vector 728.

If none of the front points $\{P_1, P_2, \ldots, P_n\}$ propagate to grid position [Q.x] when the front is propagated by one step forward, then the position Q.x is set to the grid position [Q.x]. The displacement Q.dx is set such that the target position of point Q, which is Q.x+Q.dx, corresponds to the centre of the target positions of all neighbours forming part of the front. That is:

$$Q.dx = \left[\sum_{i=1}^{n}(P_i.x + P_i.dx)\right]/n - Q.x \quad (10)$$

Figure 7C:
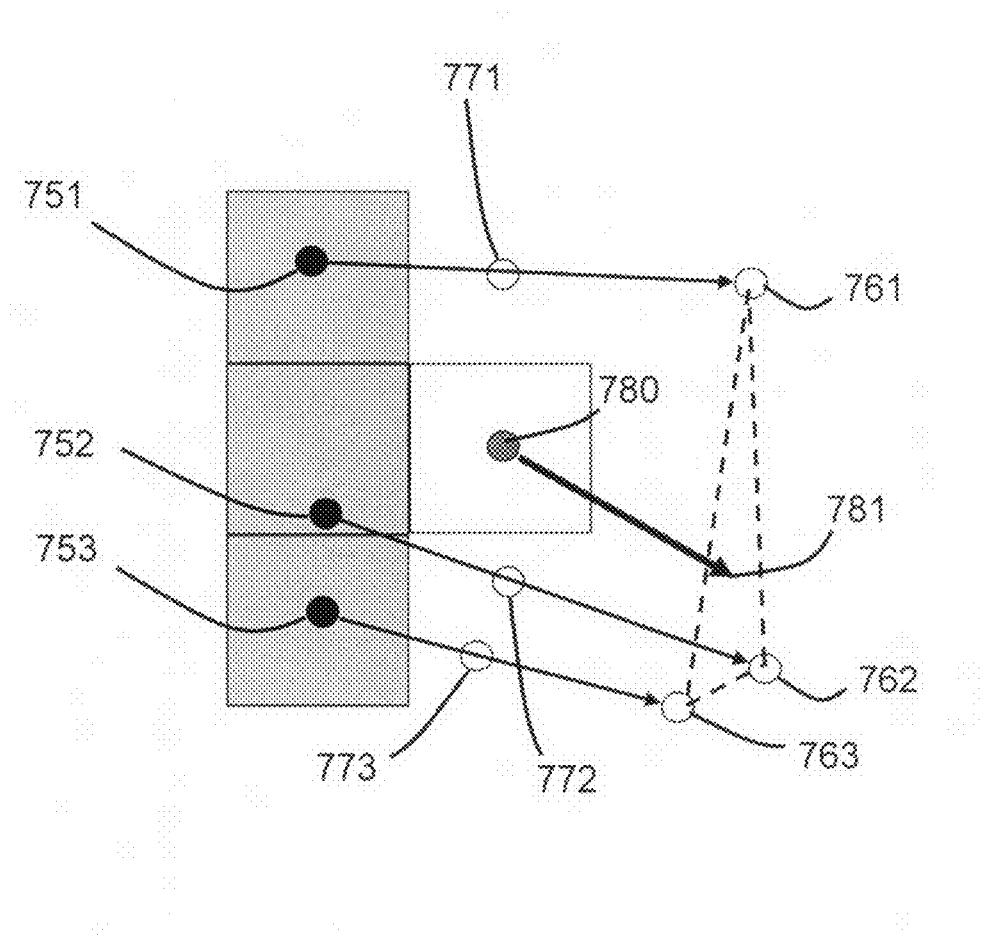

FIG. 7C illustrates a front including three front points 751, 752 and 753, and having target points 761, 762 and 763 respectively. When the front is propagated by one step forward, the front points 751, 752 and 753 propagate to positions 771, 772 and 773 respectively, none of which corresponding to point Q. Accordingly, the position Q.x is set to the grid position 780, and the displacement Q.dx is set to such that the target position 781 of point Q corresponds to the centre of the target positions 761, 762 and 763 of front points 751, 752 and 753 respectively.

Having described the update of the front displacement, single front one step forward propagation is now described. As stated above, when [P.x]≠[P.x+P.dx], that front point P is considered to be active. When at least one of a front's points P is active, then the front is said to be active. Otherwise the front is non-active. Only active fronts can propagate forward.

For front point P, P.label indicates the label L of the atlas A(x) at that front point P. As has been mentioned before, all points within a volume have same label L, and the label L=0 is the background label indicating unlabeled structures. A front point P is defined to be a simple point when the addition or removal of that front point P from the volume volume(P) does not change the digital topology of that volume volume (P). To determine whether a particular front point P is a simple point or not, the method presented in Bertrand G, "*Simple points, topological numbers and geodesic neighborhoods in cubic grids*", Pattern Recognition Letters, vol. 15, pp. 1003-1011, 1994 is preferably used. The main principle applied in that method is to determine whether the number of connected components within certain geodesic neighbourhoods is changed or not.

Figure 3:
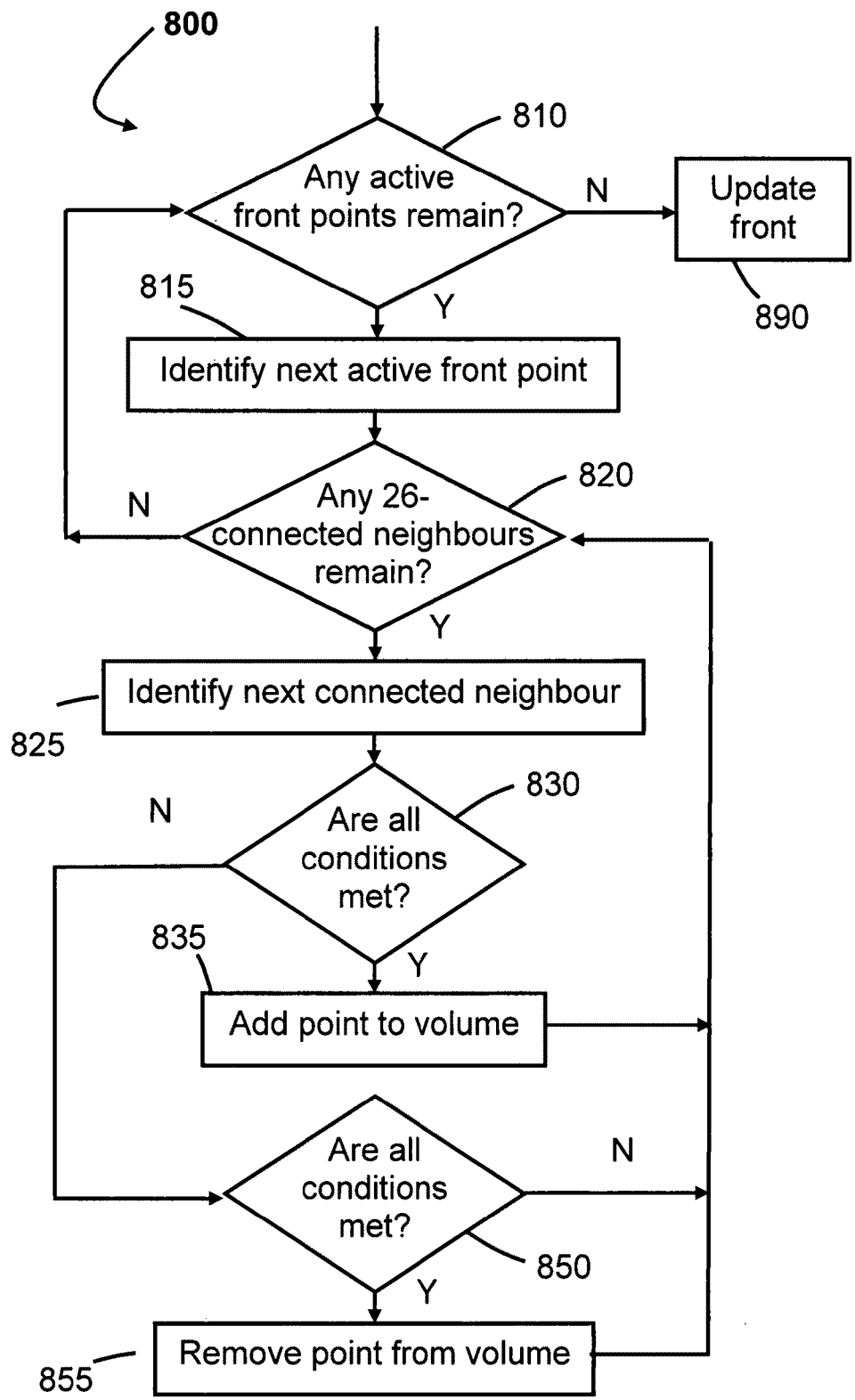
FIG. 3 shows a schematic flow diagram of a process for advancing an active front one step forward by adding and removing front points.

FIG. 3 shows a schematic flow diagram of a process 800 for advancing an active front one step forward by adding and removing front points P. The process 800 starts in step 810 where it is determined whether any active front points P remain for processing. In the case where one or more active front points P still remain, the process 800 continues to step 815 where the next active front point is identified. Step 820 then follows where it is determined whether any of the 26-connected neighbours of that active front point P remain for processing. If no more 26-connected neighbours remain for processing, then the process 800 returns to step 810 from where the next active front point P is processed.

In the case where one or more 26-connected neighbours remain for processing, the process 800 continues to step 825 where the next 26-connected neighbour is identified.

Step 830 then follows where it is determined whether:

a) the label of the preceding point pre(Q) of point Q, which is a 26-connected neighbour of the front point P under consideration, has the same label as front point P. That is pre(Q).label=P.label; and b) point Q is a simple point; and c) point Q has a label Q.label=0, that is point Q does not belong to any structure.

If it is determined in step 830 that all 3 of the above conditions are met by the 26-connected neighbour point Q, that point Q is added in step 835 to the volume volume.P. This is done by labelling point Q with the same label as front point P, hence setting Q.label=P.label. Step 835 thus corresponds to region growing.

Following step 835, the process 800 returns to step 820.

If it is determined in step 830 that not all 3 of the stated conditions are met, then the process 800 continues to step 850 where it is determined whether:

a) the label of the preceding point pre(P) of the front point P is the same as the label of the front point P under consideration. That is pre(P).label=P.label; and b) the label of the succeeding point next(P) of the front point P is that of the background (next(P).label=0), which means that the succeeding point next(P) does not presently belong to a structure; and c) point P is a simple point.

If it is determined in step 850 that all 3 of the above conditions are met by the front point P under consideration, that front point P is then in step 855 removed from its present volume volume.P by labelling point P with the background label, hence setting P.label=0. Step 855 thus corresponds to region shrinking.

Following step 855, or if it is determined in step 850 that not all 3 of the stated conditions are met, the process 800 returns to step 820 to process the remaining neighbours.

Once it is determined in step 810 that all active front points P have been processed, the process 800 continues to step 890 where the front is updated by determining the front displacements P.dx of all front points P, and in the manner described above with reference to FIGS. 7A to 7C.

The above process 800 deforms the atlas A(x) by growing and shrinking structures within the atlas A(x) in a manner that preserves topology. As the structures within the atlas A(x) are used to calculate boundary displacements, the deformation may be said to be anatomically driven. The process 800 therefore does not required for particular structures to be extracted from the image I(x).

Figure 9A:
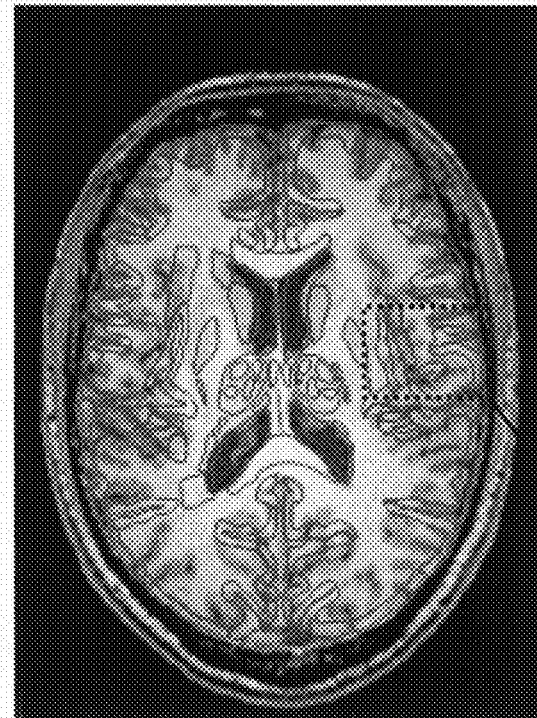
FIG. 9A shows the outlines of the brain atlas shown in FIG. 4A after that brain atlas has been warped with the method disclosed herein, with that warped brain atlas superimposed over the MRI brain image shown in FIG. 4B.
Figure 9B:
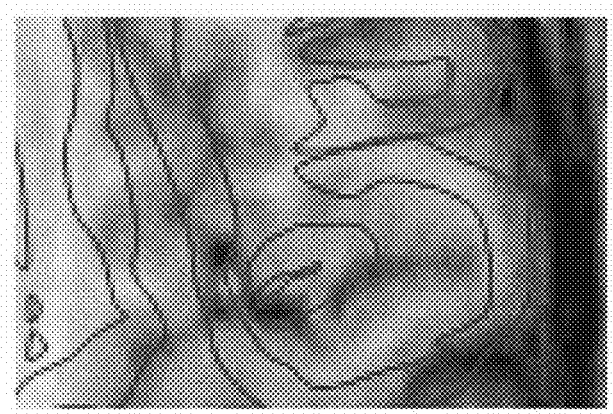
FIG. 9B shows a portion of the image of FIG. 9A magnified in order to more clearly show the structures therein.

FIG. 9A shows the outlines of the brain atlas A(x) shown in FIG. 4A after that brain atlas A(x) has been warped using the non-rigid registration of step 130, with that warped brain atlas A(x) superimposed over the MRI brain image I(x) shown in FIG. 4B. FIG. 9B shows a portion of the image of FIG. 9A magnified in order to more clearly show the result obtained through step 130.

The foregoing describes only some embodiments of the present invention, and modifications and/or changes can be made thereto without departing from the scope and spirit of the invention, the embodiments being illustrative and not restrictive.

In one further embodiment a multi-resolution strategy is adopted whereby the size of the blocks B (formed in step 131) is changed from large to small during processing. The boundary warping applied in step 133 is then applied to each block size. This multi-resolution strategy allows the non-rigid registration performed in step 130 to initially operate on large blocks B, thereby making large deformation to the structures in the atlas A(x), followed by progressively smaller blocks B, causing finer, and more accurate deformations to the structures.

We claim:

1. A method of non-rigidly registering an atlas with an image, said method comprising the steps of:

dividing a predefined domain into regular blocks, said regular blocks being hexahedrons, said atlas and said image being volumetric images defined in said predefined domain, said atlas comprising a plurality of labels L, each non-zero label L representing a labeled structure and the label L=0 representing an unlabeled structure;

calculating a boundary displacement of at least one structure in said atlas according to labels L of that structure to register that structure with an equivalent structure in said image, said calculating step comprising the sub-steps of:

calculating a displacement of centre points of each block, said displacement maximising a block similarity measure between corresponding blocks in said atlas and said image; and calculating said boundary displacement by calculating a displacement for points on said boundary of said structure by interpolating said displacements of neighbouring centre points; and warping the boundary of said structure in said atlas according to said boundary displacement using topology preserving front propagation of boundary points of said structure in said atlas according to labels L.

2. The method according to claim 1, wherein said topology preserving propagation of boundary points comprises adding points to and removing points from the boundary of said structure.

3. The method according to claim 2, wherein only points not belonging to other structures are added to said structure.

4. An apparatus for non-rigidly registering an atlas with an image, said apparatus comprising:
- means for dividing a predefined domain into regular blocks, said regular blocks being hexahedrons, said atlas and said image being volumetric images defined in said predefined domain, said atlas comprising a plurality of labels L, each non-zero label L representing a labeled structure and the label L=0 representing an unlabeled structure;
- means for calculating a boundary displacement of at least one structure in said atlas to register that structure with an equivalent structure in said image, said calculating means comprising:
- means for calculating a displacement of centre points of each block, said displacement maximising a block similarity measure between corresponding blocks in said atlas and said image; and
- means for calculating said boundary displacement by calculating a displacement for points on said boundary of said structure by interpolating said displacements of neighbouring centre points; and
- means for warping the boundary of said structure in said atlas according to said boundary displacement using topology preserving front propagation of boundary points of said structure in said atlas according to labels L.

5. The apparatus according to claim 4, wherein said topology preserving propagation of boundary points comprises adding points to and removing points from the boundary of said structure.

6. The apparatus according to claim 5, wherein only points not belonging to other structures are added to said structure.

7. A computer program product including a non-transitory computer readable medium having recorded thereon a computer program for execution on a computer system for non-rigidly registering an atlas with an image, said computer program comprising:
- code for dividing a predefined domain into regular blocks, said regular blocks being hexahedrons, said atlas and said image being volumetric images defined in said predefined domain, said atlas comprising a plurality of labels L, each non-zero label L representing a labeled structure and the label L=0 representing an unlabeled structure;
- code for calculating a boundary displacement of at least one structure in said atlas to register that structure with an equivalent structure in said image, said calculating code comprising:
- code for calculating a displacement of centre points of each block, said displacement maximising a block similarity measure between corresponding blocks in said atlas and said image; and
- code for calculating said boundary displacement by calculating a displacement for points on said boundary of said structure by interpolating said displacements of neighbouring centre points; and
- code for warping the boundary of said structure in said atlas according to said boundary displacement using topology preserving propagation of boundary points of said structure.

8. The computer program product according to claim 7, wherein said topology preserving propagation of boundary points comprises adding points to and removing points from the boundary of said structure.

9. The computer program product according to claim 8, wherein only points not belonging to other structures are added to said structure.

10. The method according to claim 1, further comprising:
- pre-processing said image to remove features in said image that are not part of the object modelled in said atlas; and
- aligning said atlas roughly to said image using a global affine transformation.

11. The method according to claim 1, wherein said atlas is a brain atlas, and said image is obtained using magnetic resonance imaging (MRI).

12. The apparatus according to claim 4, further comprising:
- means for pre-processing said image to remove features in said image that are not part of the object modelled in said atlas; and
- means for aligning said atlas roughly to said image using a global affine transformation.

13. The apparatus according to claim 4, wherein said atlas is a brain atlas, and said image is obtained using magnetic resonance imaging (MRI).

14. The computer program product according to claim 7, further comprising:
- code for pre-processing said image to remove features in said image that are not part of the object modelled in said atlas; and
- code for aligning said atlas roughly to said image using a global affine transformation.

15. The computer program product according to claim 7, wherein said atlas is a brain atlas, and said image is obtained using magnetic resonance imaging (MRI).

* * * * *